United States Patent [19]

Rush

[11] Patent Number: 4,502,012
[45] Date of Patent: Feb. 26, 1985

[54] METHOD OF DISCHARGING AN AEROSOL CONTAINER TO MEASURE CHARGE BUILDUP ON THE CONTAINER

[75] Inventor: Elton E. Rush, Bartlesville, Okla.

[73] Assignee: Phillips Petroleum Company, Bartlesville, Okla.

[21] Appl. No.: 427,225

[22] Filed: Sep. 29, 1982

Related U.S. Application Data

[62] Division of Ser. No. 210,504, Nov. 26, 1980.

[51] Int. Cl.³ .............................................. G01N 27/60
[52] U.S. Cl. .................................................... 324/452
[58] Field of Search ................. 324/452, 457, 72.5, 324/71.3, 424; 200/144 AP, 148 R, 148 G; 222/80, 5, 83.5, 3, 81; 361/212, 213; 310/310, 311, 308, 309

[56] References Cited

U.S. PATENT DOCUMENTS

| | | | |
|---|---|---|---|
| 2,479,801 | 8/1949 | Woodworth | 222/5 |
| 2,492,493 | 12/1949 | Misson | 310/310 |
| 2,574,284 | 11/1951 | Prochazka | 310/310 |
| 2,955,182 | 10/1960 | Caswell et al. | 200/148 G |
| 3,191,077 | 6/1965 | Marks et al. | 310/308 |
| 3,194,436 | 7/1965 | Jaynes | 222/83.5 |
| 3,297,887 | 1/1967 | Marks | 310/308 |
| 3,303,968 | 2/1967 | Compère | 222/83.5 |
| 3,717,791 | 2/1973 | Hezl et al. | 361/212 |
| 3,749,976 | 7/1973 | Colyn | 315/206 |
| 3,761,746 | 9/1973 | Adler | 310/311 |
| 3,821,507 | 6/1974 | Bratkowski et al. | 200/148 R |
| 3,828,976 | 8/1974 | Sidelinker | 222/83.5 |
| 3,858,015 | 12/1974 | Deno | 200/148 R |
| 3,926,340 | 12/1975 | Tygenhof | 222/83.5 |
| 4,293,749 | 10/1981 | Kishi et al. | 200/144 AP |
| 4,321,546 | 3/1982 | Schneider, Jr. | 324/452 |

Primary Examiner—Stewart J. Levy
Assistant Examiner—Kevin D. O'Shea

[57] ABSTRACT

A container is positioned on an electrically insulated support and pierced by a spring actuated piercing device while a stream of gas flows adjacent the support.

6 Claims, 9 Drawing Figures

METHOD OF DISCHARGING AN AEROSOL CONTAINER TO MEASURE CHARGE BUILDUP ON THE CONTAINER

This application is a division of application Ser. No. 210,504, filed Nov. 26, 1980.

BACKGROUND OF THE INVENTION

In one aspect, the present invention relates to preventing the fouling of electrical insulators. In another aspect, the invention relates to devices useful in positioning and/or piercing a container.

In yet another aspect, the invention relates to a device useful in measuring charge buildup on an aerosol container as its contents are discharged.

Fluorocarbons have been widely replaced by flammable gases, such as propane and butane for pressurizing containers. A possible hazard in using hydrocarbon propellants for pressurizing containers is their flammability. The release of hydrocarbon propellants from a pressurized container into the atmosphere can lead to a combustible mixture of hydrocarbon and oxygen.

The sudden release of propellant and contents from an aerosol container charged with hydrocarbon propellant may exacerbate the danger of combustion by creating a static electrical charge on the container, which may discharge to a nearby ground and cause ignition of the hydrocarbon/air mixture. The industry is thus interested in measuring the electrical charge developed on a container by the sudden discharge of hydrocarbon propellant and contents from the container so that the combustion risk can be evaluated and reduced or eliminated.

For quantitative data, it would be extremely desirable to provide an apparatus for piercing a uniform-sized hole in a container in a uniform manner. For safety, it would be desirable that the device not provide an ignition source for the discharging hydrocarbon propellant. Because suddenly discharging the contents of an aerosol container is a messy procedure, a self-cleaning device would be extremely desirable. It would be further desirable to maintain the container in electrical isolation during discharge of the contents so that the developed charge could be drawn off the container and measured. It would be even further desirable to prevent the contents of the container from coming into contact with the container or its supporting structure and neutralizing or draining off the charge developed on the container and its supporting structure during the discharge of the container contents. Simplicity of structure, ease of maintenance, and sturdiness would also be attributes of such a device.

OBJECTS OF THE INVENTION

It is thus an object of this invention to provide a device for reliably positioning a container.

It is another object of this invention to provide a means for maintaining two conductive bodies in electrical isolation in an environment conducive to the formation of conductive bridges between the conductive bodies.

It is another object of this invention to provide a non-sparking device for piercing a container.

It is another object of this invention to provide a triggering mechanism for reliably actuating a piercing device.

It is further an object of this invention to provide methods for discharging the contents of a pressurized container and maintaining a pair of conductors in electrical isolation in an environment conducive to the formation of conducting deposits between the conductors.

SUMMARY OF THE INVENTION

According to one aspect of the invention, an apparatus comprises a means for positioning a container or the like and a means for conveying a stream of gas across at least one electrical insulator which protrudes from the means for positioning the container. The stream of gas prevents fouling of the electrical insulator and thus maintains electrical isolation of the positioning means.

According to another aspect of the invention, a device for clamping a container or the like has a pair of stops positioned closely adjacent an edge thereof and a jaw movable along a line which perpendicularly bisects a line drawn between the pair of stops. The device is well suited for positioning a generally cylindrical container so that a portion of the container overlaps an edge of the support. On discharge of the container, contact between the contents of the container and the container and its contacting structures are mitigated.

According to another aspect of the invention, a triggering mechanism comprises a cam and an arm each pivotally mounted to a dowel. The cam is biased in one direction, and the arm is biased with lesser strength in the other direction. The arm is provided with a means for engaging the cam so that it can be cocked under the force of the cam. Upon actuation, the arm is propelled by the force of the cam to a striking position and rebounds to a withdrawn position. Rebound of the arm substantially mitigates contact between the discharging contents of a container and arm.

In another aspect, the device for piercing a container comprises a block, an electrical insulator protruding away from the block, a means for conveying a flow of gas into contact with the electrical insulator, a means associated with the block for positioning a container, and a means associated with the block for piercing a hole through the sidewall of the container.

In another aspect, a pressurized container is discharged by supporting the container on a structure spaced apart from the earth by at least one electrical insulator, flowing a stream of gas past the at least one electrical insulator, piercing the pressurized container with a piercing device, and allowing the contents of the container to discharge while the at least one gas flows past the electrical insulator.

In yet another aspect of the invention, a method for preventing electrical flow between a pair of spaced apart conductive materials in flow communication with an environment conducive to the formation of conductive deposits between the pair of spaced apart conducting materials is provided comprising flowing a stream of at least one clean gas between the pair of spaced apart conductive materials and into the environment conducive to the formation of conductive deposits.

BRIEF DESCRIPTION OF THE DRAWINGS

FIG. 1 is a pictorial representation illustrating certain features of the present invention.

FIG. 2 is a plan view of the invention as shown in FIG. 1 with portions thereof broken away or taken in cross section.

FIG. 3 is a side view of the apparatus as shown in FIG. 2 taken along the indicated lines, in partial cross section and with portions of the apparatus broken away.

FIG. 8 is a cross sectional view of a portion of the apparatus of FIG. 3.

DETAILED DESCRIPTION OF THE INVENTION

Figure 1:
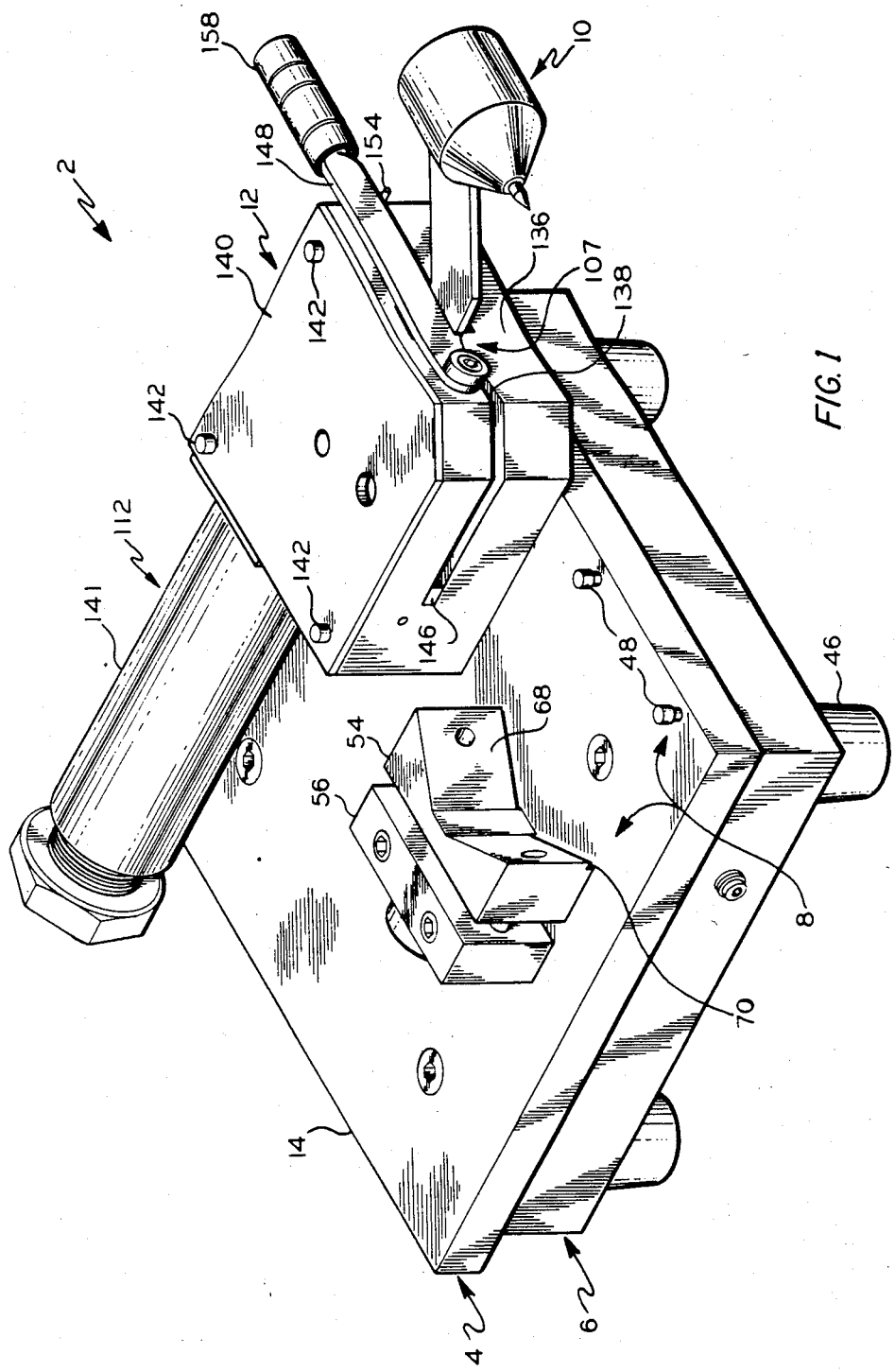

With reference to FIG. 1, a device 2 comprises a support means 4 mounted on a means 6 for maintaining isolation of the support means 4 from the earth. A means 8 for positioning a container, a means 10 for piercing a container and a triggering mechanism 12 cooperate with the support means 4.

Figure 3:
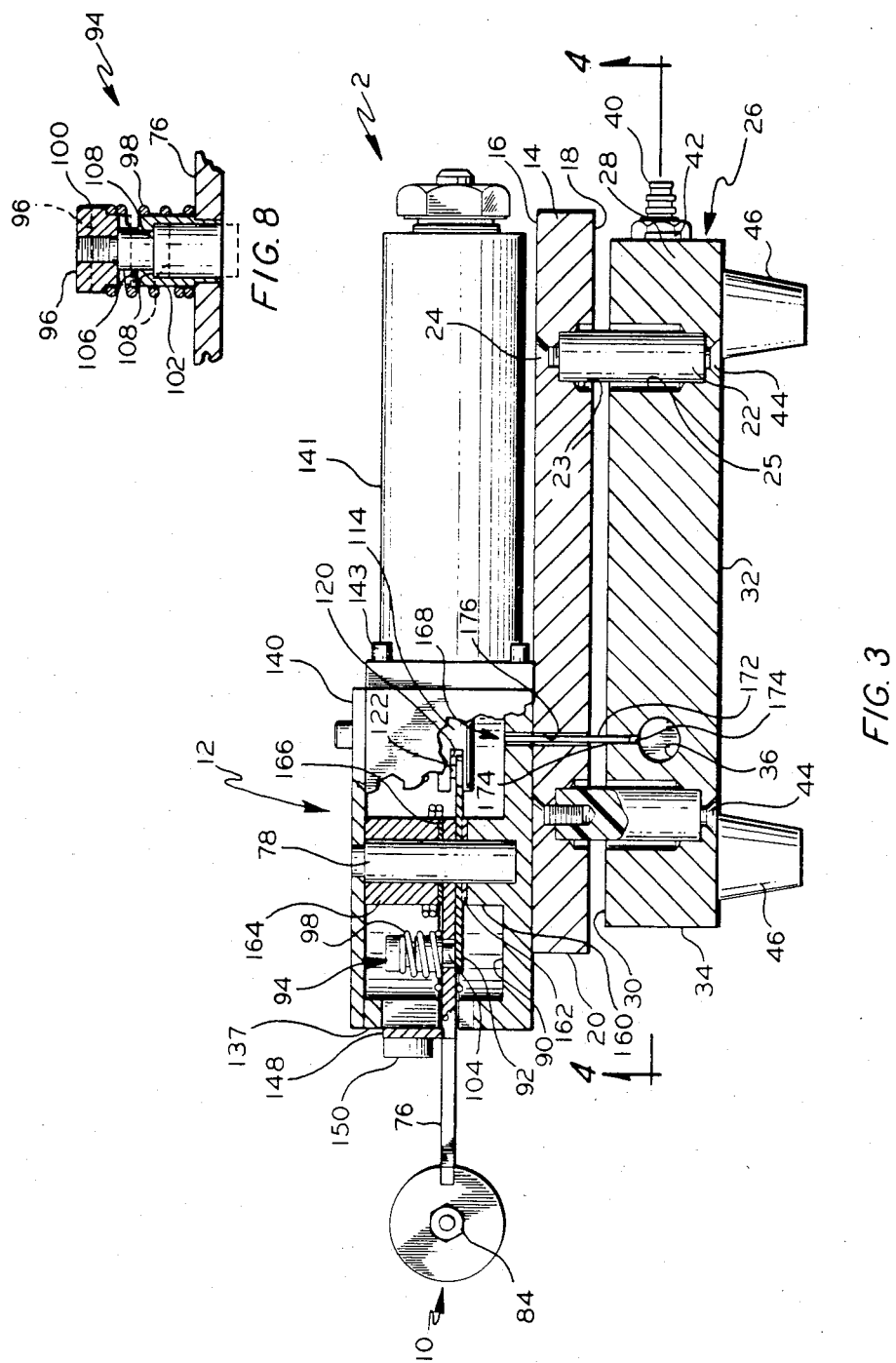

Preferably, the support means 4 has a block structure such as illustrated plate 14 for ease of manufacture. The plate 14 can be constructed of any suitable material. Relatively non-corrosive materials such as aluminum or stainless steel are preferred. As best shown by FIG. 3, the plate 14 has a first generally planar surface 16, an oppositely facing second generally planar surface 18 and at least one edge surface 20. At least one electrical insulator 22 protrudes away from the second generally planar surface 18 of plate 14. Preferably, four electrical insulators 22 are employed, one protruding from the second surface of the plate 14 in each quadrant of the plate. The electrical insulators 22 can be made from any suitable dielectric material, and can have any desired shape. Polytetrafluoroethylene in a cylindrical shape has been employed with good results. The electrical insulator 22 is affixed to the plate 14 by any suitable means. As best shown in FIG. 3, the electrical insulator is affixed to the plate 14 by a screw 24, extending through a borehole in the plate 14 and engaging the insulator 22. The insulator 22 rests in a cavity 23. The insulators 22 maintain the plate 14 in electrical isolation with respect to the ground.

Figure 4:
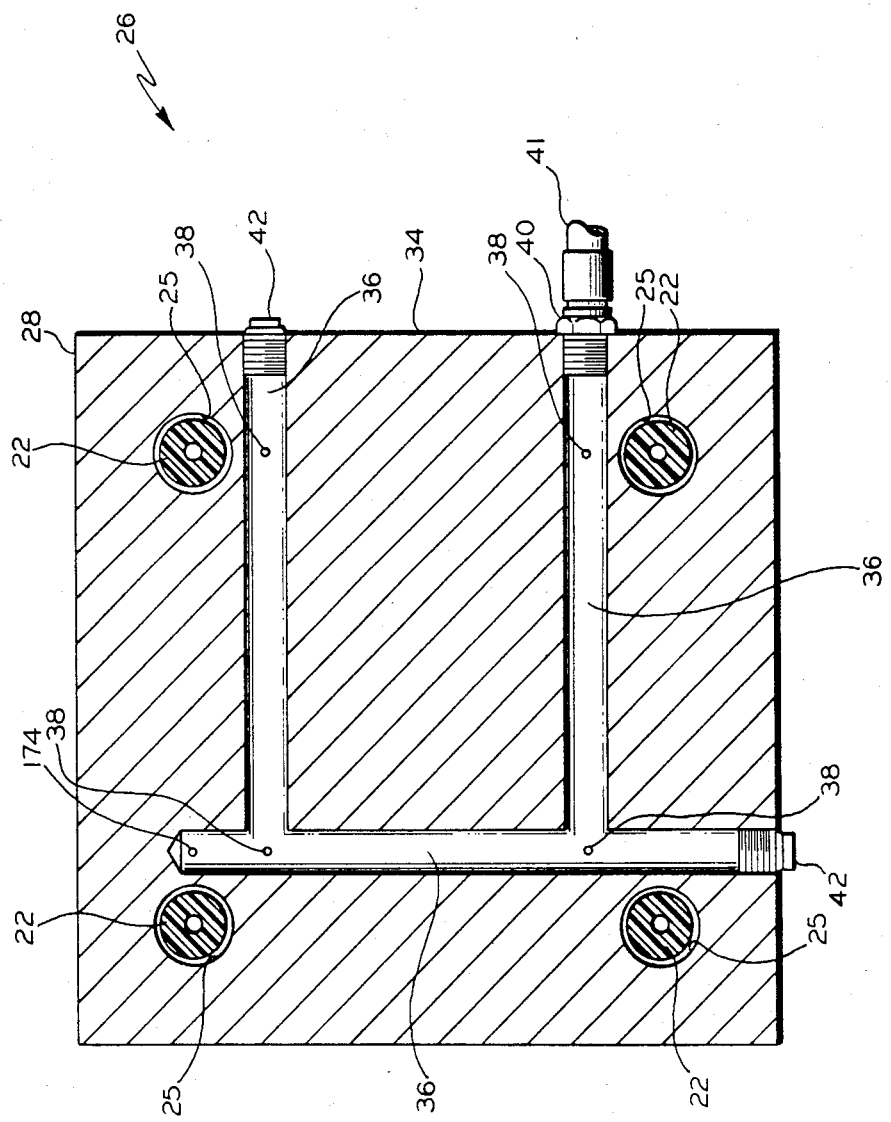
FIG. 4 is a cross sectional view of a portion of the apparatus as shown in FIG. 3 taken along the indicated lines.

To prevent fouling of the electrical insulators 22, the device 2, as shown in FIG. 3, is provided with a means 26 for conveying a stream of gas into contact with the electrical insulators 22. As shown, a body defining a flow path, such as block 28 is positioned by the electrical insulators 22 in a spaced apart relationship with the plate 14. Preferably, the block 28 has a first generally planar surface 30 and oppositely facing second generally planar surface 32 and an edge surface 34, for ease of fabrication. As illustrated, the first generally planar surface 30 of the block 28 is in spaced apart juxtaposition with the second planar surface 18 of the plate 14. Desirably, the second generally planar surface 18 of the plate 14 extends past the first generally planar surface 30 of the block 28, so as to overlap and provide a roof structure for the block 28 to shield it from discharging container contents. As shown in FIG. 4, the block 28 is provided with at least one passage 36 therethrough. The passage 36 opens through the first generally planar surface 30 of the block 28 toward the second generally planar surface 18 of the plate 14. As shown, apertures 38 define the openings. Preferably, the apertures 38 are positioned adjacent the insulators 22 and so that the insulators 22 are between the apertures 38 and the edge surface 34 of the block 28. As shown, each quadrant of the block 28 is provided with at least one aperture 38. For ease of fabrication, it is preferred that the passage 36 extend from the edge surface 34 of the block 28. A hose fitting 40 is positioned in the passage 36 where it opens onto the edge surface 34 for engagement with a hose 41. Plugs 42 block other openings formed during fabrication of the passage 36 onto the edge surface 34 of the block 28. When the apparatus is being utilized, the passage 36 is in flow communication with a source of compressed gas via the hose 41 extending from the fitting 40.

The block 28 can be made of any suitable material. Preferably a relatively dense material, such as carbon steel or stainless steel is employed. It is desirable that the block 28 have sufficient mass to provide the device 2 with table-top stability. For example, a suitable weight for the block 28 is about 10 pounds for piercing small holes in containers having about 1/10 to about 5 pounds of contents and pressurized with propane and/or butane.

As shown best in FIG. 3, the insulator 22 is affixed to the block 28 by a screw 44, although any suitable means can be utilized. Preferably, each insulator rests in a cavity 25 in the block 28. The distance separating the block 28 from the plate 14 can be any distance sufficient to prevent electrical flow between the plate 14 and the block 28 when a container positioned on the plate is discharged. It will be appreciated however that large distances between the plate and the block will require a greater flow of gases through the apertures 38 to prevent materials from entering to between the block 28 and the plate 14 during discharge of a container. For that reason, it is preferred that the block 28 be separated from the plate 14 by a distance of from about 1/16 to about 3/32 inch, by at least one insulator 22.

If desired, the block 28 can be mounted on legs, such as chassis means 46 as shown in FIG. 1 formed from a suitable material such as rubber.

Figure 2:
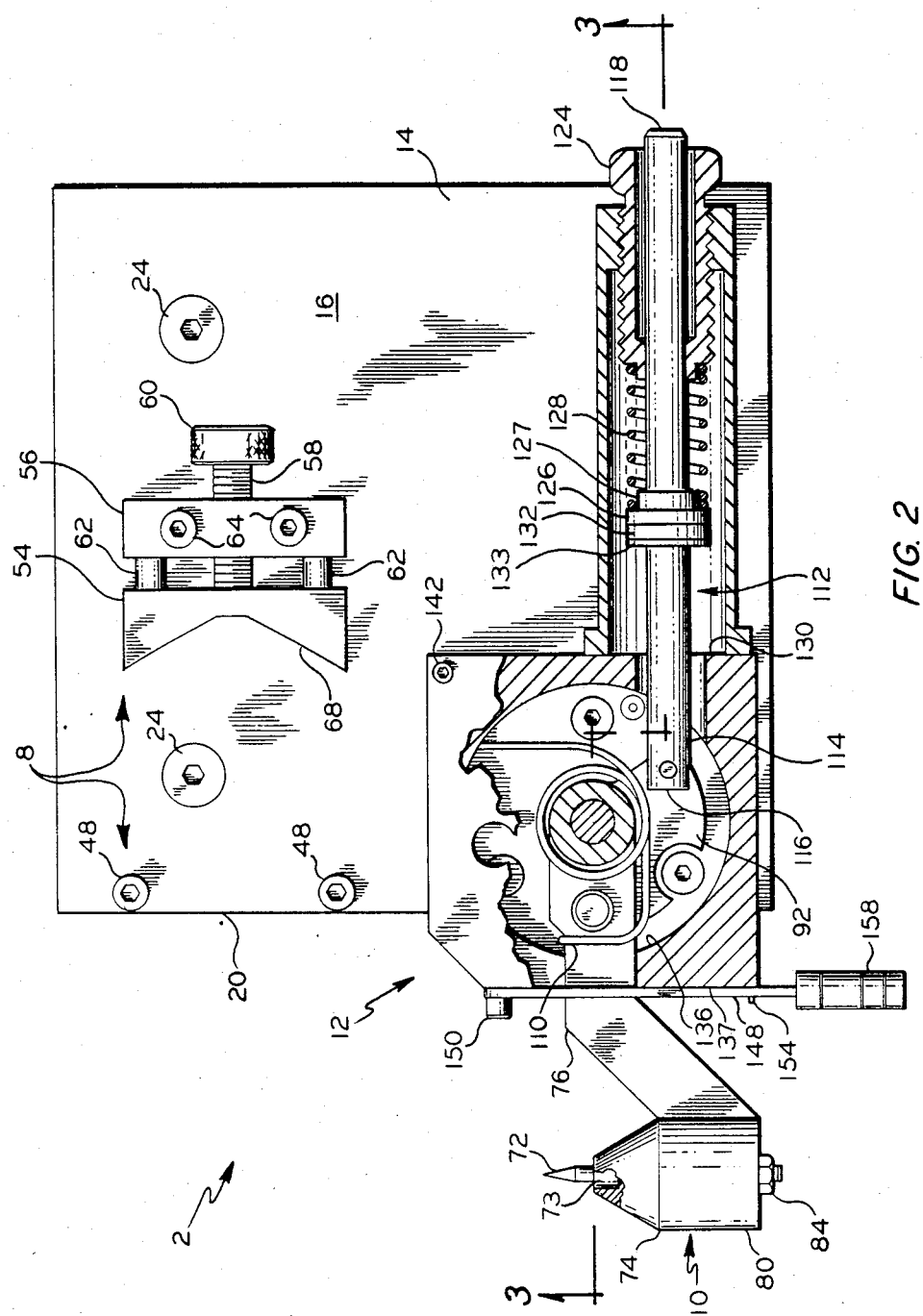
Figure 5:
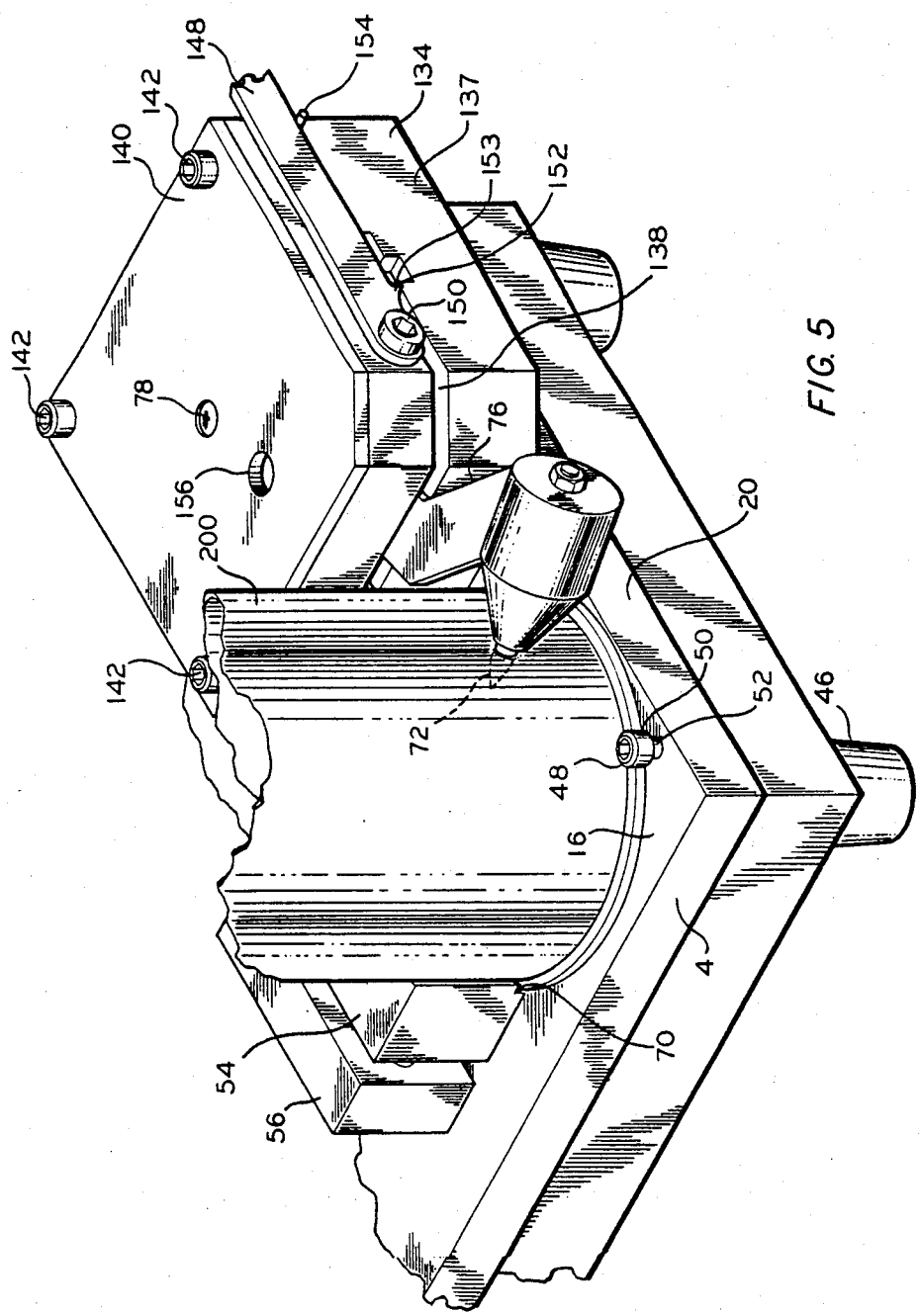
FIG. 5 is a fragment of a pictorial representation illustrating certain features of the present invention.
Figure 6:
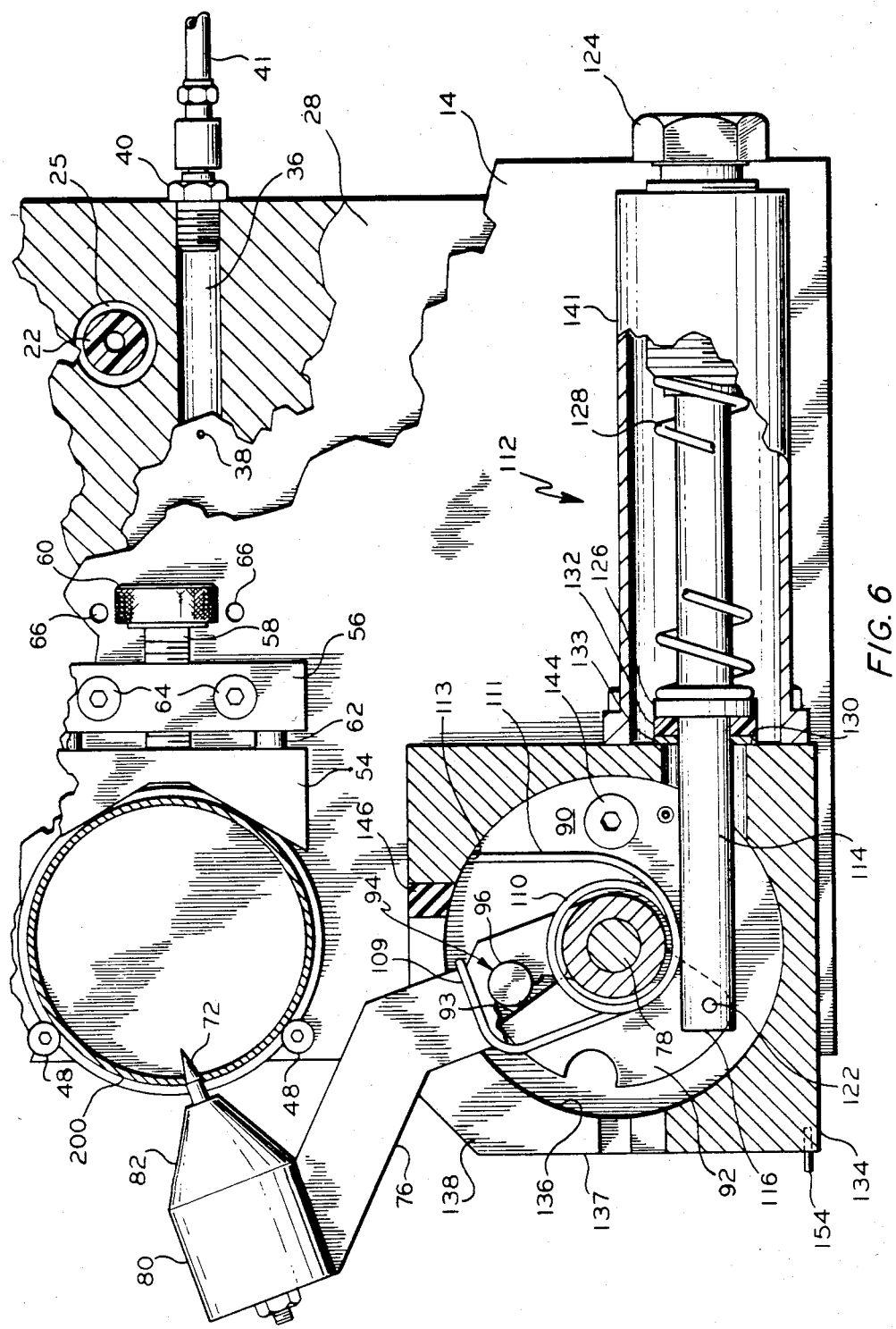
FIG. 6 is a plan view of the apparatus as shown in FIG. 5 with portions of the apparatus broken away or taken in partial cross section to show detail.

Referring to FIG. 2 the means 8 for positioning a container comprises a pair of spaced apart stops 48 positioned adjacent the edge surface 20 of the plate 14 and protruding generally normally from the first generally planar surface 16 of the plate 14. Preferably, as best shown in FIG. 5, each stop 48 has a head 50 and a shank 52 and is partially screwed into the plate 14 to form a notch between the head 50 and the first generally planar surface 16 of the plate 14 for receipt of a container rim. As shown by FIG. 2, a movable jaw 54 is mounted to the first generally planar surface 16 of the plate 14 for linear movement along a line which perpendicularly bisects a line drawn between the pair of stops 48. As shown, a body such as block 56 is affixed to the plate 14 at a distance from the pair of stops 48. A screw 58 is threadably mounted in a passage through the block 56 which is in alignment with the line which perpendicularly bisects a line drawn between the pair of stops. The screw 58 has a first end and a second end with a head 60 at its first end and is in cooperation with the movable jaw 54 at its second end. A pair of studs 62, if desired, can extend from the jaw 54 to slidable engagement with passages through the block 56 for added rigidity. The block 56 is mounted to the plate 14 by any suitable means. As shown, a pair of screws 64 join the block 56 to the plate 14 via screw-receiving taps 66. As shown in FIG. 6, the plate 14 can be provided with more than one set of taps 66. The arrangement is well suited for positioning a container having a generally cylindrical sidewall in an orientation so that its longitudinal axis is normally disposed with respect to the first surface 16 of the plate 14.

The jaw 54 preferably is provided with a generally V-shaped face 68 so as to provide at least two-point contact when urged against the side wall of a cylindrical container having cross sectional dimensions of about the same magnitude as that of the jaw. This configuration is desirable from the standpoint of stability. It is also preferred that the jaw face 68 be provided with a notch or recess 70 at its lower edge adjacent the plate 14 as shown by FIG. 1 to reliably engage the rim of a container. The positioning assembly can be constructed of any suitable material, for example, aluminum, which has been employed with good results.

Figure 7:
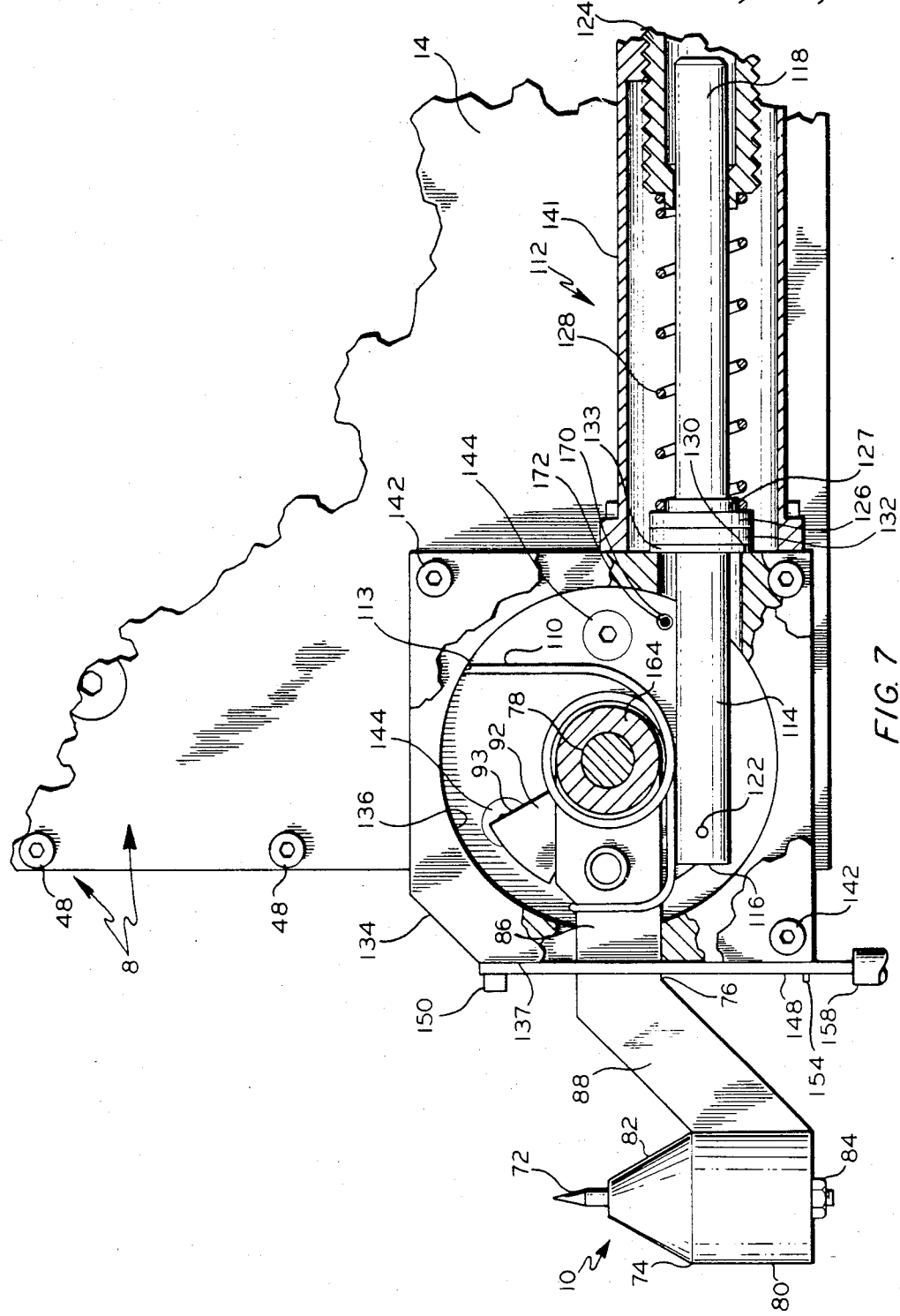
FIG. 7 is a plan view taken in partial cross section and with portions of the housing broken away illustrating certain features of the present invention.
Figure 9:
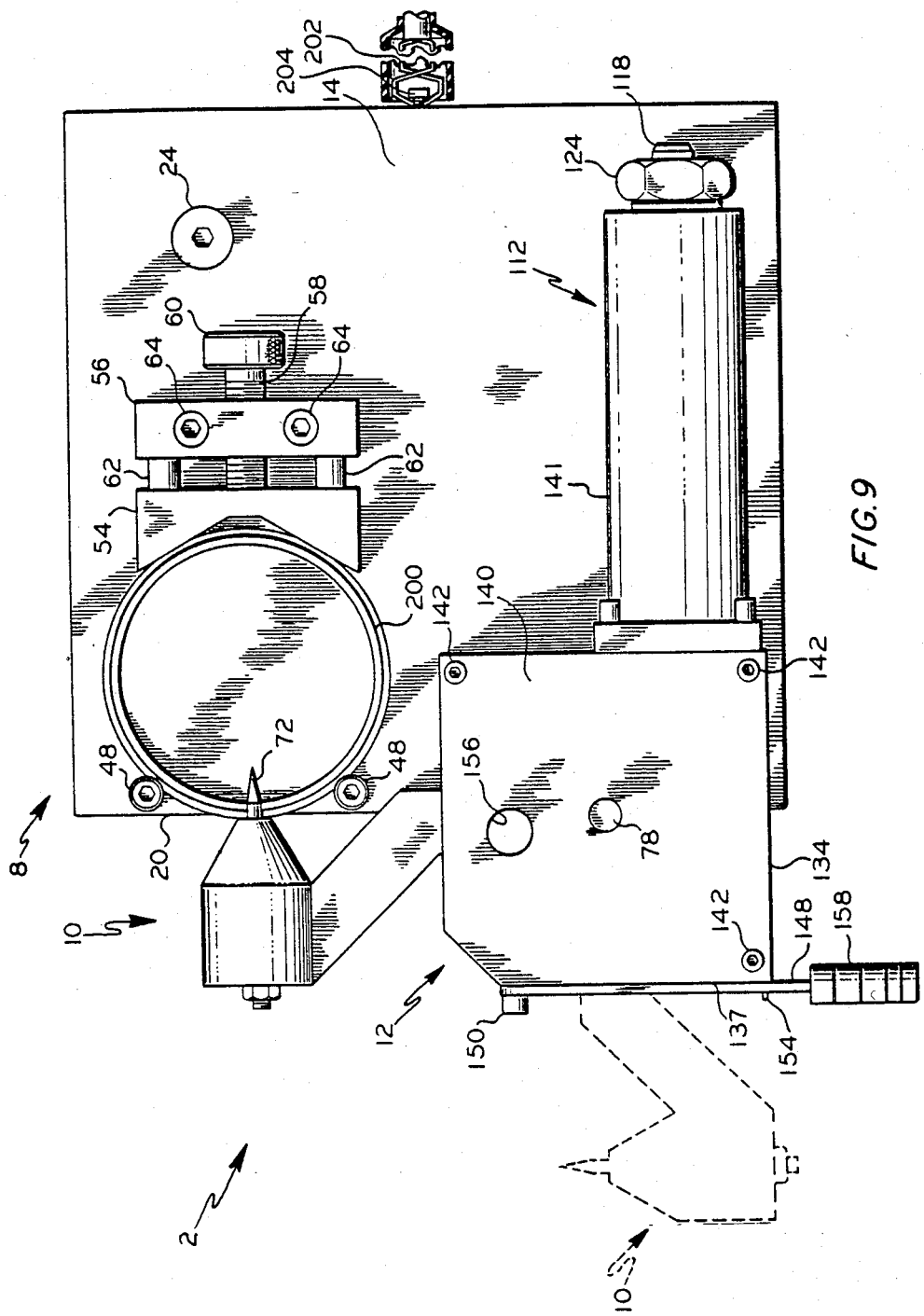
FIG. 9 is a plan view of one embodiment of the present invention.

With reference to FIG. 7, the piercing means 10 comprises a point 72 mounted on a head 74 which is pivotally mounted via an arm 76 to a dowel 78. The dowel 78 is mounted fixedly with respect to the plate 14. The point 72 is preferably constructed of a non-sparking material such as beryllium bronze. The point should have a standardized largest diameter so as to pierce a uniform hole in the sidewall of a cylindrical container. For example, points with diameters of 0.125 and 0.187 inch have been employed successfully. As shown, the head 74 has a generally cylindrical portion 80 and a generally frustoconical portion 82 which converges from the generally cylindrical portion 80 toward the point 72. The point 72 is generally pin shaped with a point end and a threaded end and extends through the head along its longitudinal axis. As best shown in FIG. 2, it is affixed to the head 74 by a flange 73 adjacent its point end which abuts against a portion of the generally frustoconical portion 82 of the head 74, and a nut 84 mounted to threads at the threaded end of the point 72 urging against the cylindrical portion 80 of the head. The arm 76 is affixed to the generally cylindrical portion 80 of the head 74 such as by silver-soldering it in a groove in the cylindrical portion of the head 74. It is desirable that the arm 76 be provided with a crook or "dog leg" so as to provide sufficient clearance with the sidewall of the can when the apparatus is deployed although a more aesthetically pleasing configuration can be utilized if further desired. As shown best in FIG. 7, the arm is provided with a generally radially extending portion 86 which extends radially from the dowel 78 and a bent portion 88 which extends from the free end of the radially extending portion 86 to the cylindrical portion 80 of the head 74. The bent portion 88 of the arm 76 is bent in a direction away from the point 72. The arm 76, head 74, and point 72 are oriented so that the point has a tangential orientation with respect to the swing of the arm around the axis of the dowel 78. The arm 76 is of sufficient length so that the point swings to adjacent the means 8 for positioning a container. An apparatus having currently preferred geometry with respect to the means 8 and the means 10 as is shown in FIG. 9. A portion of a sidewall 200 of a container shown in cross-section is positioned by the means 8 even with or slightly overlapping edge 20 of the plate 14 so that a portion of the sidewall of the container extends at least to the edge of the plate 14. The dowel 78 is aligned even with or past the edge 20, so that the point 72 pierces the container along a line which generally perpendicularly bisects a line drawn between the pair of stops. The arm and head can be constructed of any suitable material, preferably a relatively dense, material, such as stainless steel. The dowel can be constructed of any suitable material, such as drill rod.

Referring to FIG. 3, the triggering mechanism 12 comprises a support plate 90 with the dowel 78 affixed thereto and extending generally normally therefrom. A cam 92 is pivotally mounted to the dowel. Referring to FIG. 6, preferably, the cam 92 has a generally sector-like shape with an arc, for example, of about 120° and is mounted to the dowel via an aperture adjacent the vertex of the sector. The arm 76 is mounted on the dowel 78 adjacent the cam 92, and extends radially from the dowel 78 past the arced edge of the cam. A means 94 is movably mounted to the arm 76 for releasably engaging the cam 92. As shown best in FIG. 8, the means 94 comprises a dog 96 slidably mounted through the arm 76 with the longitudinal axis of the dog 96 parallel to the axis of the dowel 78. The dog 96 is movable from a first position (shown in phantom in FIG. 8) which frictionally engages the cam 92 along an edge 93 shown best in FIG. 6 to a second position which is out of engagement with the cam 92. A helical spring 98 serves as means for biasing the dog 96 away from the cam 92. The spring 98 urges against an upper portion 100 of the dog 96 and against the arm 76. The dog 96 rides within a bushing 102 which is pressed fitted into an aperture 104 through the arm 76. The bushing 102 is provided with an annulus 106 at its upper end which abuts against a shoulder 108 of the dog 96 when the dog 96 is out of engagement with the cam 92.

The arm 76 and the cam 92 pivot from first positions to second positions. A latching means 107 is provided to releasably retain the arm 76 in its second position as shown in FIG. 1. The arm 76 pivots through a greater arc than the cam 92 and the first position of the arm 76 is past the first position of the cam 92 as shown in FIG. 6. A torsional spring 110 encircles the dowel 78 and serves as means for biasing the arm 76 away from the direction of the point 72 and toward its second position. The spring 110 has a first end 109 cooperating with the arm 76 and a second end 111 at a fixed position 113 with respect to the support plate 90. A means 112 for biasing the cam 92 toward its first position is provided comprising a rod 114 having a first end 116 and a second end 118 best shown in FIG. 7 pivotally attached by its first end 116 to the cam 92. A yoke 120 shown best in FIG. 3 formed in the first end 116 of the rod 114 receives an edge portion of the cam 92 which is retained in cooperation with the yoke 120 by a pin 122 pivotally affixing the cam 92 to the yoke 120 of the rod 114. The cam 92 and the rod 114 thus pivot in the same plane. A bushing 124 as shown in FIG. 7 slidably mounts the rod 114 adjacent its second end 118. The bushing 124 is positioned at a distance from the dowel 78. A flange 126 is affixed to the rod 114 between the first end 116 of the rod and the bushing 124. A helical spring 128 encircles the rod 114 and abuts the flange 126 and the bushing 124 to urge the rod toward the cam and the cam toward its first position. An annular shoulder 127 affixed to flange 126 serves to retain the spring 128 in coaxial relationship with the rod 114. The flange 126 urges against a shoulder 130 positioned at a distance from the dowel 78 when the cam reaches its first position. It is preferred that a resilient washer 132 be positioned on the rod 114 adjacent the cam side of the flange 126. The washer 132 can be formed from any suitable material such as rubber. Its working life can be improved by covering it with a metal washer 133. The bushing 124 is adjustable with respect to its distance from the dowel 78 as shown, so that the force exerted by spring 128 is adjustable.

It is preferred that the triggering mechanism be surrounded by a suitable housing designated generally in FIG. 5 by the numeral 134. From the support plate 90, (see FIG. 3) which in this embodiment serves as the housing basewall, there extends a sidewall 136 having a peripheral slot 138 therethrough. A cover 140 is mounted on the peripheral sidewall by suitable fastening devices such as screws 142. A tubular housing 141 (see FIG. 3) for the rod 114 is mounted to the peripheral sidewall 136 by suitable fastening devices such as screws 143. The bushing 124 is mounted in one end of the tubular housing 141. The housing 134 is affixed to the plate 14 by suitable fastening devices such as arrows 144, (see FIG. 7) extending through the basewall of the housing and engaging the plate 14. The arm 76 extends through the slot in the housing. The slot is provided with an enlarged gap for passage of the dog during assembly. A resilient bumper 146 (see FIG. 6) is positioned at a first end of the slot 138 to provide impact protection between the arm 76 and the sidewall 136 of the housing as the arm is propelled to its first position by the cam. Referring again to FIG. 5, a latch arm 148 is associated with the exterior surface 137 of the sidewall 136 adjacent a second end of the slot providing means for restraining the arm in its second position against movement toward its first position when the cam is engaged. The latch arm 148 is pivotally affixed to the exterior sidewall 137 of the housing 134 by a screw 150. In the cocked position, the arm 76 urges against a tooth 152 extending from the latch arm 148. Preferably, the tooth 152 is provided with a face 153 which follows an arc around the screw 150 for smooth operation of the latch arm 148. The arm 76 abuts against the face 153 when the arm is in its second position. A pin 154 is affixed to the exterior surface 137 of the sidewall 136 to provide a rest for the latch 148. The pin 154 is positioned so that the latch arm 148 is aligned with the slot 138 when the latch arm 148 contacts the pin 154. An aperture 156 through the housing cover 140 provides access for depressing the dog 96 into engagement with the cam 92. (See FIG. 3) The latch arm 148 is provided with a dielectric handle 158. (See FIG. 1) The handle 158 can be formed from any suitable dielectric material, for example Marlex ® polyethylene.

It is preferable that the arm 76 and the cam 92 fit the dowel 78 so as to avoid excessive side play. As best shown in FIG. 3, the dowel 78 rests in a cup 160 protruding from the basewall 90 of the housing 134. A washer 162 constructed from a suitable material, such as brass, is interposed between the cam 92 and the cup 160 to serve as a shim and to reduce friction between the cam 92 and the support cup 160. A spacer 164 surrounds the dowel 78 and abuts against an interior surface of the housing cover 140. A second washer 166 having the desired thickness to reduce side play is interposed between the spacer 164 and the arm 76. The washers 162 and 166 can be lubricated to reduce friction.

It is further desirable in the present invention to provide a means 168 as shown in FIG. 3 for purging the housing 134 with a suitable purge gas. As shown, a flow path extends from the passage 36 through the block 28, the plate 14 and the housing basewall 90 to the inside of the housing 134. Preferably, a tube 172 extends from an aperture 174 opening from the passage 36 onto the first surface 30 of the block 28 and into a passage 176 through the first block 14. The tube 172 is desirable to prevent aspiration of materials from the space between the block 28 and the plate 14 and into the housing 134.

Operation of the device 2 is as follows. With the hammer in the rebound position, shown in FIG. 7, a container is positioned in the means 8 and the jaw 54 moved toward the pair of stops 48 to clamp the container into position. Latch arm 148 is lifted and arm 76 is moved toward its first position until the dog 96 clears the edge 93 of the cam 92. Dog 96 is then depressed into its first position by inserting a finger or other suitable digit through the aperture 156 in the cover 140. Arm 76 is then brought back to its second position carrying with it the cam 92 by virtue of frictional engagement of the cam 92 along its edge 93 with dog 96. When the arm 76 and cam 92 are in their second positions, the latch 148 will fall by gravity and the apparatus will be in its cocked position shown in FIG. 1. Spring 128 will be compressed as shown in FIG. 2. Hose fitting 40 is connected to a suitable source of compressed gas, such as air, and gas flow begun through the passage 36. The gas flow is adjusted until sufficient gas is flowing from between the plate 14 and block 28 to flicker a match, for example. Latch arm 148 is then lifted and spring 128 expands, urging the cam 92 and arm 76 toward their respective first positions, shown in FIG. 6. Flange 126 is urged against the shoulder 130 and the cam 92 stops in its second position. The dog 96 by virtue of the spring 98 returns to its second position. The point 72 enters the sidewall 200 of the container as shown in FIGS. 5, 6 and 9, preferably along a diameter of the container. Its momentum exhausted, the point stops and then rebounds to its second position as shown in FIG. 7 due to the biasing action of torsional spring 110. The contents of the container discharge. The velocity of the gas flowing from the passage 36 is sufficient to substantially prevent contact between the discharged contents of the container and the electrical insulators. Preferably, the container is pierced adjacent the lower edge of its sidewall, as shown in FIG. 5, to insure that its contents are substantially emptied. As static charge develops on the container and its contacting structure, it is desirable that it be continuously withdrawn and stored in a capacitor, for example, for measuring purposes. This is conveniently accomplished via an electrical lead 202 connected to a screw 204 protruding from the edge surface 20 of the plate 14, as shown in FIG. 9. Due to the flow of purging gas from the device 2 and into the environment which is conducive to the formation of conductive deposits it is possible to prevent electrical flow between the plate 14 and the block 28. Soiling of the interior surfaces of the apparatus is also successfully prevented.

What is claimed is:

1. A method of discharging the contents of a pressurized container comprising:
   (a) supporting the container on a structure spaced apart from the earth by at least one electrical insulator;
   (b) flowing a stream of at least one gas past the at least one electrical insulator;
   (c) piercing the pressurized container with a piercing device and allowing contents of the container to discharge while the at least one gas flows past the at least one electrical insulator.

2. A method as in claim 1 wherein the contents of the container are discharged in a direction away from the structure.

3. A method as in claim 2 wherein the stream of at least one gas flows past the at least one electrical insulator in a direction away from the structure.

4. A method as in claim 3 wherein the velocity of the at least one gas is sufficient to substantially prevent contact between the discharged contents of the container and the at least one electrical insulator.

5. A method as in claim 4 further comprising measuring the electrical charge developed on the container by the discharge of the contents of the container.

6. A method for preventing an electrical flow between a pair of spaced apart conducting materials in flow communication with the discharge of an aerosol container comprising flowing a stream of air between the pair of spaced apart conductive materials and into the discharge.

* * * * *